United States Patent
Beckert et al.

(10) Patent No.: US 6,948,653 B2
(45) Date of Patent: Sep. 27, 2005

(54) HAZARDOUS MATERIAL DETECTION SYSTEM FOR USE WITH MAIL AND OTHER OBJECTS

(75) Inventors: John T. Beckert, Endicott, NY (US); Daniel M. Hutchinson, Vienna, VA (US); Daniel G. Rice, Owego, NY (US); William S. Terry, Barton, NY (US)

(73) Assignee: Lockheed Martin Corporation, Bethesda, MD (US)

( * ) Notice: Subject to any disclaimer, the term of this patent is extended or adjusted under 35 U.S.C. 154(b) by 0 days.

(21) Appl. No.: 10/282,868

(22) Filed: Oct. 29, 2002

(65) Prior Publication Data

US 2004/0026491 A1 Feb. 12, 2004

Related U.S. Application Data

(60) Provisional application No. 60/350,977, filed on Oct. 29, 2001.

(51) Int. Cl.[7] .................................................. B65G 11/04
(52) U.S. Cl. ....................... 232/45; 232/17; 73/864.33
(58) Field of Search .......................... 232/17, 43.3, 45; 73/864.33; 588/200; 422/50, 119

(56) References Cited

U.S. PATENT DOCUMENTS

| | | |
|---|---|---|
| 3,915,339 A | 10/1975 | Matson |
| 3,998,101 A | 12/1976 | Fagan et al. |
| 4,580,440 A | 4/1986 | Reid et al. |
| 4,718,268 A | 1/1988 | Reid et al. |
| 4,764,351 A | 8/1988 | Hennebert et al. |
| 4,987,767 A | 1/1991 | Corrigan et al. |
| 5,065,615 A * | 11/1991 | Hill .......................... 73/29.01 |
| 5,109,691 A | 5/1992 | Corrigan et al. |
| 5,212,993 A | 5/1993 | Mayer |
| 5,322,603 A | 6/1994 | Kameda et al. |
| 5,345,809 A | 9/1994 | Corrigan et al. |
| 5,465,607 A | 11/1995 | Corrigan et al. |
| 5,470,546 A | 11/1995 | Hall |
| 5,585,575 A | 12/1996 | Corrigan et al. |
| 5,591,117 A | 1/1997 | Zelno |

(Continued)

FOREIGN PATENT DOCUMENTS

| | | |
|---|---|---|
| EP | 0169057 | 1/1986 |
| FR | 2797953 | 3/2001 |
| JP | 02159554 | 12/1988 |
| WO | WO 91/09307 | 6/1991 |

OTHER PUBLICATIONS

U.S. Postal Service Emergency Preparedness Plan for Protecting Postal Employees and Postal Customers from Exposure to Biohazardous Material and for Ensuring Mail Security Against Bioterror Attacks; Mar. 6, 2002; published by USPS.

(Continued)

Primary Examiner—William L. Miller
(74) Attorney, Agent, or Firm—Perkins Smith & Cohen LLP; Jacob N. Erlich; Peter J. Borghetti

(57) ABSTRACT

A portable detection system (10) for hazardous materials including explosives and infectious or hazardous biological agents readily adapted to conventional mail collection boxes (12), rural mailboxes (100) and the like. The system includes a fan (14) and a sensor (16). The fan (14) provides sufficient airflow to circulate the air within a mailbox such that the internal air after coming in contact with the contents is directed the sensor for analysis. The air quality can be determined visually (137), audibly (138), or electronically (139). Consequently once such detection is made and the air is verified as being safe, the contents can be removed safely. If it is determined that the air contains some type of hazardous material, further steps can be taken to specifically locate the source of such hazardous material. An alternative embodiment includes a filter (15) to improve fan efficiency.

44 Claims, 9 Drawing Sheets

U.S. PATENT DOCUMENTS

| | | |
|---|---|---|
| 5,700,426 A | 12/1997 | Schmitthaeusler et al. |
| 5,841,038 A | 11/1998 | Volz |
| 5,859,362 A | 1/1999 | Neudorfl et al. |
| 5,942,699 A | 8/1999 | Ornath et al. |
| 6,074,608 A | 6/2000 | Matz |
| 6,159,422 A | 12/2000 | Graves et al. |
| 6,183,950 B1 | 2/2001 | Madonna et al. |
| 6,295,860 B1 | 10/2001 | Sakairi et al. |
| 6,324,927 B1 | 12/2001 | Ornath et al. |
| 6,742,703 B2 | 6/2004 | Esakov et al. ................. 232/45 |
| 2001/0029793 A1 | 10/2001 | Moler et al. |
| 2002/0124664 A1 | 9/2002 | Call et al. |
| 2002/0126008 A1 | 9/2002 | Lopez et al. |
| 2003/0085348 A1 | 5/2003 | Megerle |
| 2003/0136203 A1 * | 7/2003 | Yoon ....................... 73/864.33 |
| 2003/0222132 A1 | 12/2003 | Esakov et al. ................. 232/30 |
| 2004/0020267 A1 * | 2/2004 | Megerle ..................... 73/31.03 |
| 2004/0024278 A1 * | 2/2004 | Megerle ..................... 588/200 |
| 2004/0045342 A1 * | 3/2004 | Jones et al. .................... 73/37 |

OTHER PUBLICATIONS

International Search Report, Oct. 21, 2003, PCT/US02/34375 (12078–197PCT).

WO 03/081214, Published PCT International Application, Publication Date Oct. 2, 2003, PCT/US02/34375 (12078–197PCT).

WO 03/085373, Published PCT International Application, Publication Date Oct. 16, 2003, PCT/US02/35984 (12078–154PCT).

* cited by examiner

HAZARDOUS MATERIAL DETECTION SYSTEM FOR USE WITH MAIL AND OTHER OBJECTS

CROSS REFERENCE TO RELATED APPLICATIONS

This application claims priority of Provisional Application No. 60/350,977, entitled "HAZARDOUS MATERIAL DETECTION SYSTEM FOR USE WITH MAIL AND OTHER OBJECTS" filed on Oct. 29, 2001, and which is incorporated herein by reference.

BACKGROUND OF THE INVENTION

This invention relates generally to the detection of hazardous material, and, more particularly to a first line of defense in the detection of hazardous material associated with the collection or delivery of mail or other objects.

Recently there has been increased awareness of the potential for large-scale introduction of hazardous materials, that is, either explosives or infectious or hazardous biological organisms to create chaos or to harm an intended set of victims. One potential delivery method that terrorists or other criminals utilize to deliver such hazardous materials is through the mail or other form of a delivery. In so doing damage, not only is damage incurred by the intended victims, but also to any set of potential victims that may be in a position of handling such objects as the mail during the delivery or distribution process.

There is currently technology available to law enforcement organizations to detect the presence of both explosive and infectious or hazardous biological threats. Such test materials generally are sensitive to specific hazardous materials and are utilized when directly put in contact with such hazardous materials. To date, however, there is a lack of early detection of such hazardous material especially in the early phases of mail handling or processing. Additionally, there is a lack of detection at the rural mailbox or home or office delivery point. Recently, a rash of pipe bombs have detonated or been discovered undetonated in mailboxes. Several innocent people have been injured by these pipe bombs. It is believed that in some instances these pipe bombs are not even entering the postal system, but are being directly delivered by the bomber to the addresses. Systems in place today do not deal with detection prior to entering into the formal distribution process or at the final destination. Thus, all along the distribution process potential non-intended victims are being subjected to hazardous material carried by, for example, letter or package mail or are lying in wait for the unsuspecting resident to venture to the mailbox for possibly the last time.

SUMMARY OF THE INVENTION

The present invention provides a hazardous material detection system, which is capable of being used in the early detection of such hazardous material. Although not limited thereto its primary use may occur in the mail collection system prior to the distribution of such mail or other objects for its intended victims or use may occur at the final destination where the perpetrators have circumvented the postal service making a personal delivery directly to the intended victims. Such hazardous material may be in the form of bio-chemical substances, such as anthrax, or explosives. The advantages of the present invention are achieved by the embodiments of the invention described below.

In the mail handling or distribution network it is preferred that the hazardous bio-chemical agents or explosives which may be contained within mail or packages are detected at the collection point such as in mail collection boxes or the like. There are a number of embodiments of the present invention described in detail below to perform such detection at an early stage and include, for example, detection systems capable of operating with bulk mail or other such objects wherein the detection system is reusable, disposable and/or removably affixed to a container. The detection system may also be in the form of a portable detection system capable of being removably used with containing means.

At the other end of the mail distribution network is the resident or business that receives the mail or packages at a remote, unsecure location, such as a rural mailbox. Portable detection systems similar to those disclosed for mail collection boxes or the like are adaptable to rural mailboxes or other remote, unsecure mail delivery points.

The detection systems may vary and can include biochemical detecting agents that are capable of detecting DNA sequence or protein unique to the bio-agent through its interaction with test molecules. Further systems may involve the utilization of biological tissue-based systems in which a bio-agent or bio-toxin affects live cells causing them to undergo some measurable response that can be detected. Further detection can be by chemical mass spectrometry methods that works by breaking down a sample into its components and comparing their relative weights to those known bio-agents and other molecules.

For a better understanding of the present invention, together with other and further objects thereof, reference is made to the accompanying drawings and detailed description.

DETAILED DESCRIPTION OF THE INVENTION

Figure 1A:
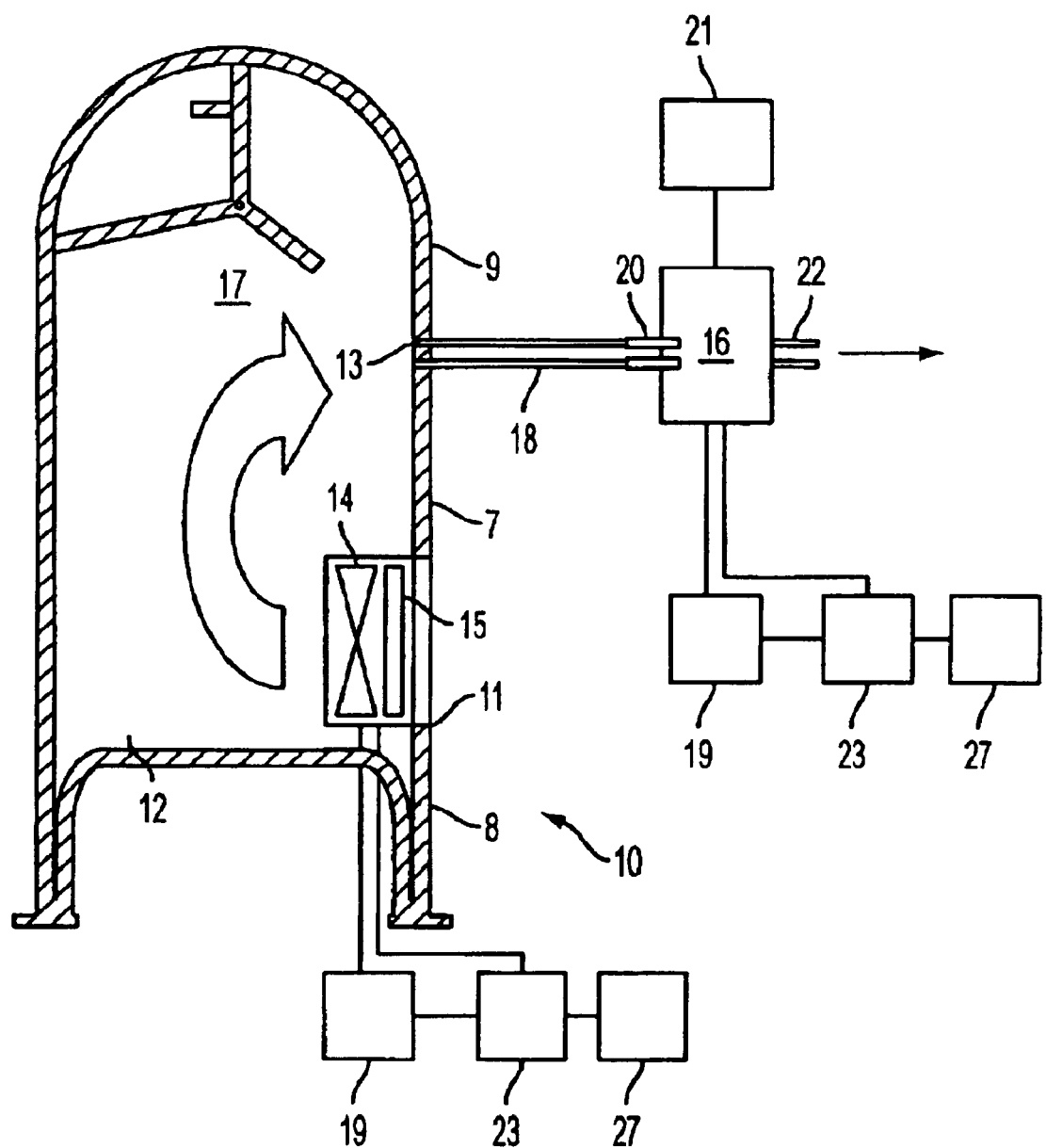
FIG. 1A is a sectional view of a conventional mail collection box illustrating a preferred embodiment of the present invention with the fan and filter unit being positioned within the mail collection box.

One embodiment of the present invention is set forth in FIG. 1A and can be used with bulk products or objects such as mail. This embodiment of the invention is in the form of a portable detection system 10 that can be readily adapted to be used with a conventional mail collection box 12. As shown in FIG. 1A, the mail collection box 12 is modified to contain a conventional fan 14 and a filter 15 used in conjunction with a portable detection device 16.

The mail collection box 12 can be further modified with holes, slots or the like located in the sidewalls to act as an air inlet 11 or sensor outlet 13. The air inlet 11 forms a fluid passage from the atmosphere outside the mail collection box 12 with the interior or chamber 17 of the mail collection box 12. The air inlet 11 is optional when air circulation within the mail collection box 12 is adequate to sense particulates by the portable detection device 16. The sensor outlet 13 forms a fluid passage from the chamber 17 to the atmosphere outside the mail collection box 12. The sensor outlet 13 is sized to receive the portable detection device 16 external to the mail collection box 12 (discussed in detail below). Alternatively, the air inlet 11 and sensor outlet 13 may include a conventional one-way valve or equivalent to prevent air from uncontrollably entering or leaving the chamber 17.

The fan 14 and portable detection device 16 are powered by a conventional alternating (ac) or direct current (dc) power source 19. The power to the fan 14 and portable detection device 16 is activated by a conventional switch 23. The switch 23 can be a keyed or keyless (remote) on-off switch for extra security. It should be noted that switch 23 can be any switch known to one of ordinary skill in the art. In the case where a battery is the power source 19, the battery can be an integrated component of the fan 14 or portable detection device 16 units operably connected to the switch 23 and the fan 14 or the switch 23 and the portable detection device 16. With the battery as an integrated component of the units, the operator only needs to activate the switch 23 without hooking up an auxiliary battery or other power sources thereby eliminating the requirement that the operator transport the auxiliary battery or other power source to a mail collection box 12. An additional advantage of an integral battery is the flexibility when used in conjunction with a keyless or remote switch. The operator can conduct the air quality test a safe distance away from the mail collection box 12. Once the air sampling is complete, the fan 14 and portable detection device 16 can be shut off at a distance allowing the disturbed air and particulates in the chamber 17 to settle. In this instance, the risk of exposure to hazardous agents to the operator is significantly reduced.

However, there are situations that warrant auxiliary power sources, such as when battery life or power output is inadequate. The situation may be further complicated when replacing a battery in a fan 14 or portable detection device 16 requires the operator to enter into the chamber 17 prior to air quality testing, thereby possibly exposing the operator to hazardous agents. Also, it may be more difficult to gain access to the fan 14 or portable detection device 16 when the units are in the chamber 17. Alternatively, an ac or dc connector (not shown) can be provided in conjunction with or in place of the power supply 19.

The key or remote activated on-off switch provides a level of security that only authorized personnel operate the fan 14 or portable detection device 16. The additional security measure not only reduces the risk of releasing hazardous agents into the environment but also conserves battery life and reduces maintenance. The key or remote activated on-off switch can be adapted for used in a fan 14 and a portable detection device 16 that are either attached to the interior or exterior of the mail collection box 12.

Figure 1B:
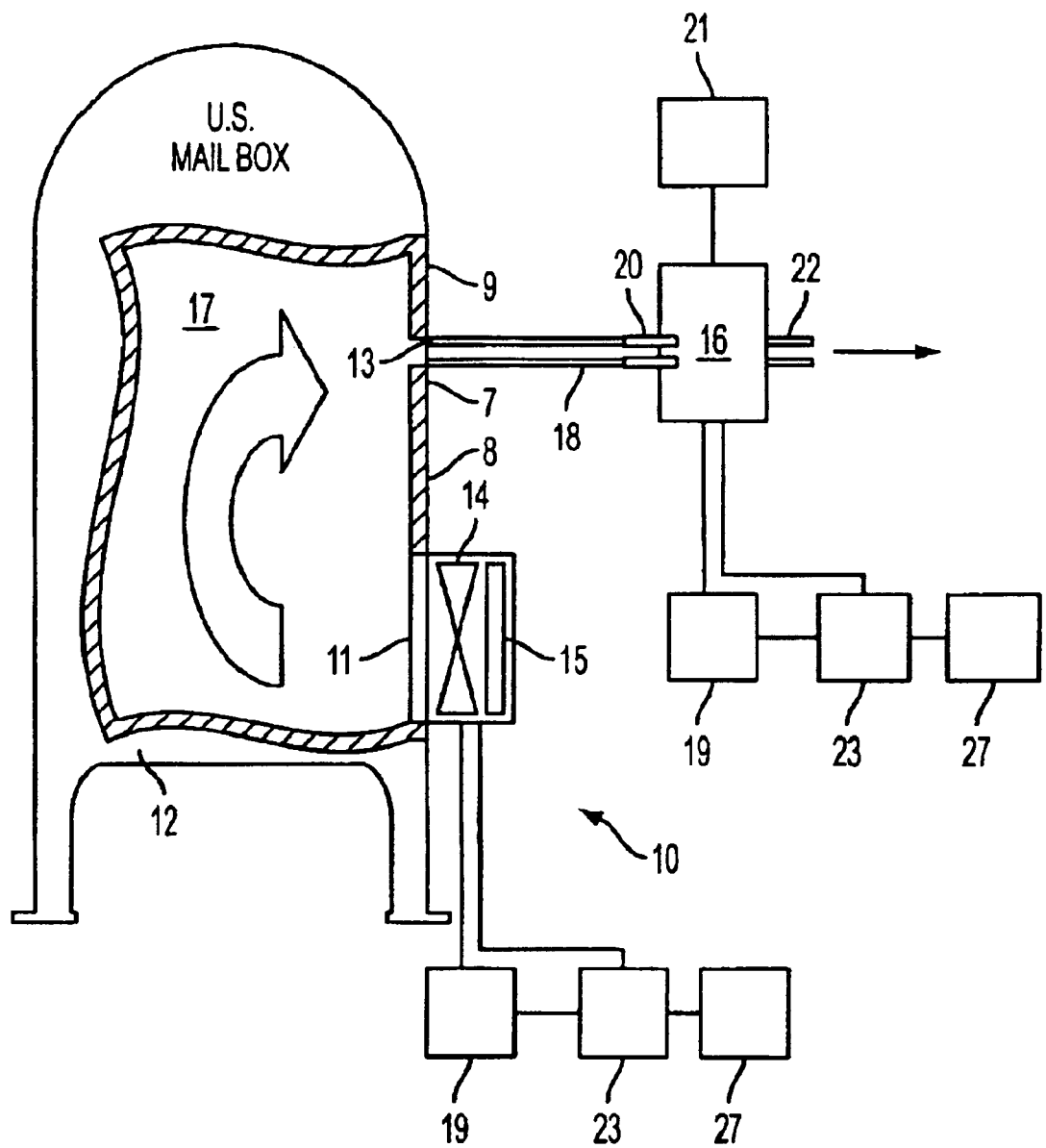
FIG. 1B is a partial sectional view of a conventional mail collection box illustrating an alternative embodiment of the present invention shown in FIG. 1A with the fan and filter unit being positioned outside the mail collection box.

In an alternative embodiment illustrated in FIG. 1B, the fan 14 and the filter 15 are in fluid communication with the interior or chamber 17 of the mail collection box 12 from the exterior of the box 12 through the air inlets 11 in any of the side walls. The fan 14 and filter 15 can be removably attached to the exterior of the box 12 by conventional means adjacent to the air inlets 11. In this embodiment, the fan 14 and the filter 15 blows air into the chamber 17 of the mail collection box 12. The fan 14 and the filter 15 are, preferably, installed only during the air quality analysis process and then removed and stored.

The fan 14 and the filter 15 provide sufficient air flow to circulate the air within the chamber 17 such that the air, after coming in contact with the contents of mail collection box 12, is directed to a portable detection device 16 in fluid communication with the chamber 17. In the present invention, a hose or outlet 18 interconnects the portable detection device 16 with the chamber 17 through the sensor outlet 13. Particulates on the outer surface of the contents become airborne particulates in the air stream created by the fan 14 when agitated by the circulation of the chamber air. Additionally, the air stream may be sufficient to agitate the contents causing particulates contained within the contents to be liberated into the air stream. The filter 15 is removable for cleaning or replacement to assure efficient performance of the fan 14. However, the filter 15 can be an optional feature where the fan operation is hindered by insufficient air mass flow due to unmanageable filter clogging.

Prior to the removal of any objects or mail from collection mail collection box 12, the fan 14 and portable detection device 16 are started. The portable detection device 16 samples the air collected from within the chamber 17 with conventional type sampler units described below. The portable detection device 16 includes a sample collection port 20 to receive sampled air from the mail collection box 12 through the sensor outlet 13. The portable detection device 16 further includes a filtered output port 22 to exhaust cleaned sampled air into the surrounding environment. Consequently once such detection or sampling is made and the chamber air is verified as being safe, the contents of mail collection box 12 can be removed safely. If it is determined that the air within mail collection box 12 may contain some type of hazardous material, an indication is given either by an electronic signal or audio alarm or visual alarm or combination can be generated by an alarm system 21 for further steps to be taken to specifically locate the source of such hazardous material.

As described above, a switch 23 turns on the fan 14 and portable detection device 16. The air can be sampled for a predetermined time based on the manufacturer specifications of the conventional portable detection device. The predetermined sampling time is, preferably, measured by the operator. Alternatively, a timer 27 can be added to the circuitry, as shown in FIGS. 1A and 1B, to precisely measure the air sampling time interval and shut off the fan 14 and portable detection device at the appropriate times.

Figure 1C:
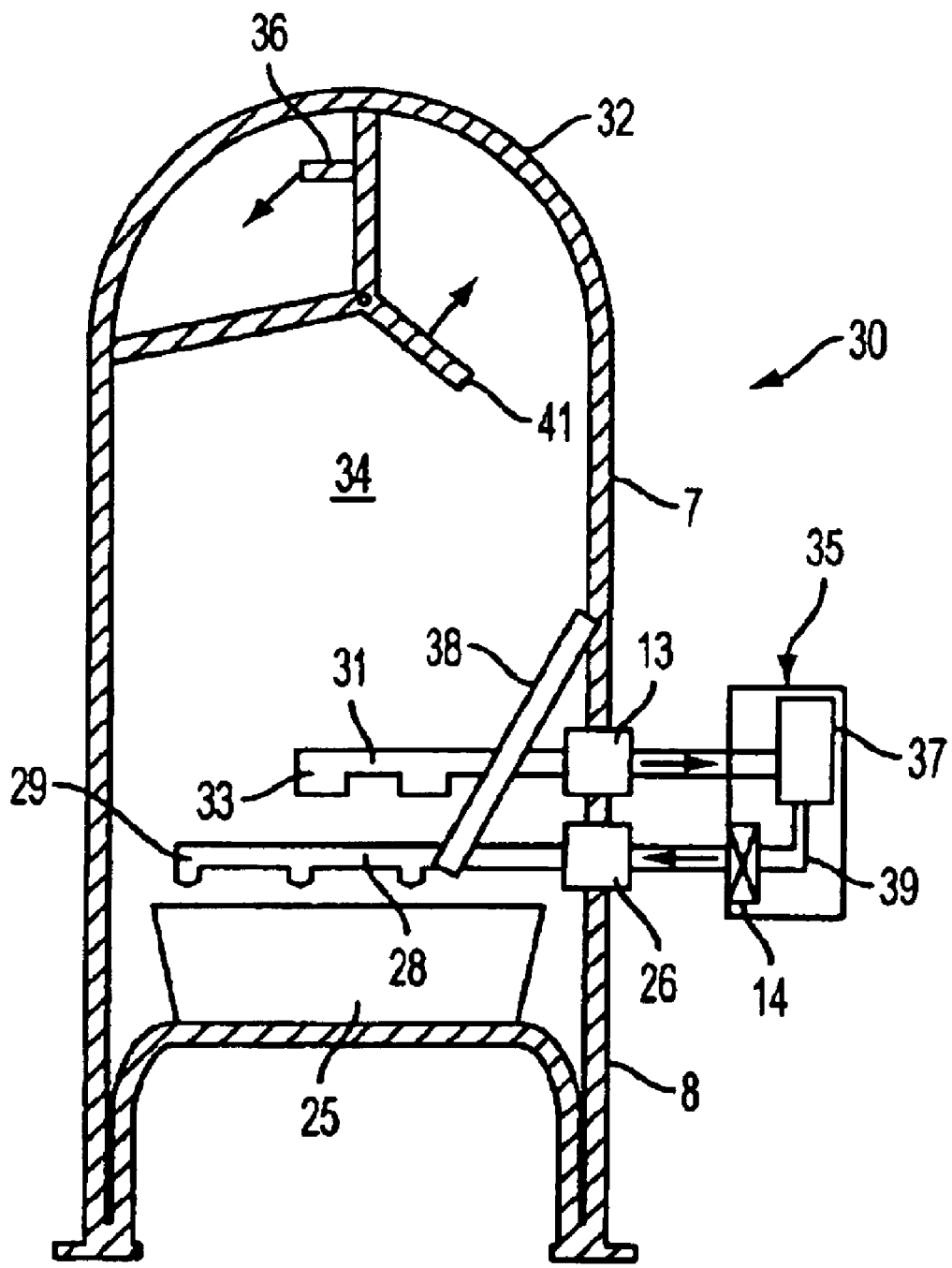
FIG. 1C is a sectional view of a conventional mail collection box illustrating another alternative embodiment of the present invention shown in FIG. 1A with the fan and filter unit being housed in one unit.

FIG. 1C shows another alternative embodiment of a contaminant detection system 30 for use in conjunction with a mail collection receptacle 32 having a chamber 34 for receiving deposited mail articles. System 30 is intended for use with a standard mailbox having a user operated door 36 for receiving deposited mail articles. Closure of door 36 by a user causes mail articles to slide down rear portion 41 and to drop into a standard mail flat 25 after being deflected by a slide for shield 38.

System 30 is adapted to be located outside of the mail collection receptacle 32 and includes a mobile test unit 35. Test unit 35 is coupled to the chamber 34 by an inlet port 26 and an outlet port 13 affixed to the sidewall 7 of mail collection receptacle 32. Ambient air within chamber 34 is stimulated by fan 14, which forces air through inlet port 26 and through a distribution channel 28. Distribution Channel 28 includes one or more nozzles 29 which direct the incoming air flow in the direction of any deposited mail to articles located in mail flat 25. In the embodiment shown, nozzles 29 are directed downwardly from above mail flat 25. The incoming air flow is thereby pressurized in one or more air streams to provide more concentrated mixing action for any particulate contaminants, located on deposited mail articles, into the ambient air of chamber 34.

Once any particular contamination is mixed in the ambient air of chamber 34, the air may then be tested for the presence of such particulate contaminants. For this purpose, ambient air is drawn from chamber 34 through outlet port 13 to air sampling unit 37. The collection of ambient air is enhanced by a collection channel 31 having one or more inlets 33 which collect air from different portions of chamber 34.

For the purpose of safety, it is desirable to avoid distribution of ambient air from chamber 34 outside of mail collection receptacle 32. For this purpose, air sampling unit 37 may be constructed as a closed loop system, in which air withdrawn from chamber 34 through output port 13 is returned from air sampling unit 37 to inlet fan 14 as shown by return conduit 39. Air that is returned in this manner is preferably filtered first to prevent the spread of any particulate contaminants. A single power source and on-off switch can be used to operate the fan 14 and air sampling unit 37 or each component can have its own power source and switch. The power supply and on-off switch are similar to those described above and known to one of ordinary skill of the art.

It should be noted that the air inlet and sensor outlet shown positioned near the bottom 8 and top 9 along the sidewalls 7, respectively, can be positioned along any sidewall 7 at any height, on the bottom 8, or the top 9 of the mail collection box 12. The fan 14 and the portable detection device 16 can be positioned internal or exterior the mail collection box in any combination, such as fan 14 on the exterior and the portable detection device 16 on the interior.

In order to obtain a clearer understanding of the present invention it is first necessary to recognize that there are a number of currently available systems including biochemical systems, biological tissue—based systems and chemical mass spectrometry systems which are available to detect infectious or hazardous biological materials as well as explosives. Any of these commercially available detection systems that detect particulates typically ranging in size from approximately 2 to 10 microns would be appropriate for use a detection system. Examples of technologies and systems for detection compatible with the present invention include fluorescence aerosol particle sizing, flow cytometry, and flame photometry (discussed in detail below).

Fluorescence aerosol particle sizing (FPS) is a combination of Aerodynamic Particle Sizing technology and fluorescence technology (UV-LIF) in a single system. Commercial sources include Pacific Scientific Instruments (PSI), TSI Particle Instruments, Bristol Industrial & Res Assoc. LTD (BIRAL), and Computing Devices Canada.

Flow cytometry measures particle sizes and counts particles in liquid suspensions through use of laser scattering. Typically, the sample is also treated with fluorescent dye that reacts with biological material. Commercial sources include Becton Dickerson, Coulter, Los Alamos Laboratories, and Lawrence Livermore Laboratories.

Flame photometry, also known as flame atomic emission spectrometry, for biological detection is based on the phosphorous content of biological material that is visible to flame photometry. Gas chromatography or gas-liquid chromatography involves the principle that a gas passed over a solid or liquid surface to which it has some tendency to bind will be slowed compared to a gas which does not bind. Commercial sources include Cy Terra Corporation.

Figure 1D:
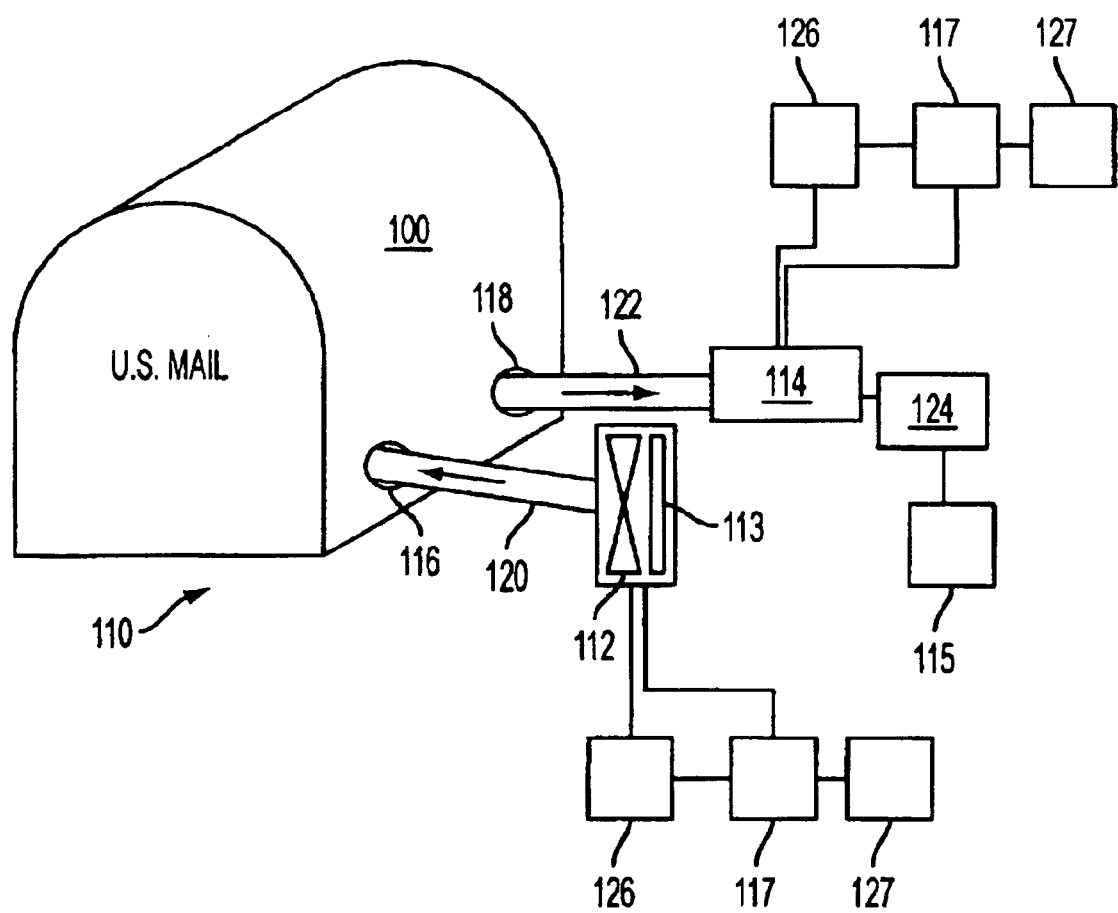
FIG. 1D is a schematic, pictorial representation of the present invention used in conjunction with a business, personal or private mailbox.
Figure 2A:
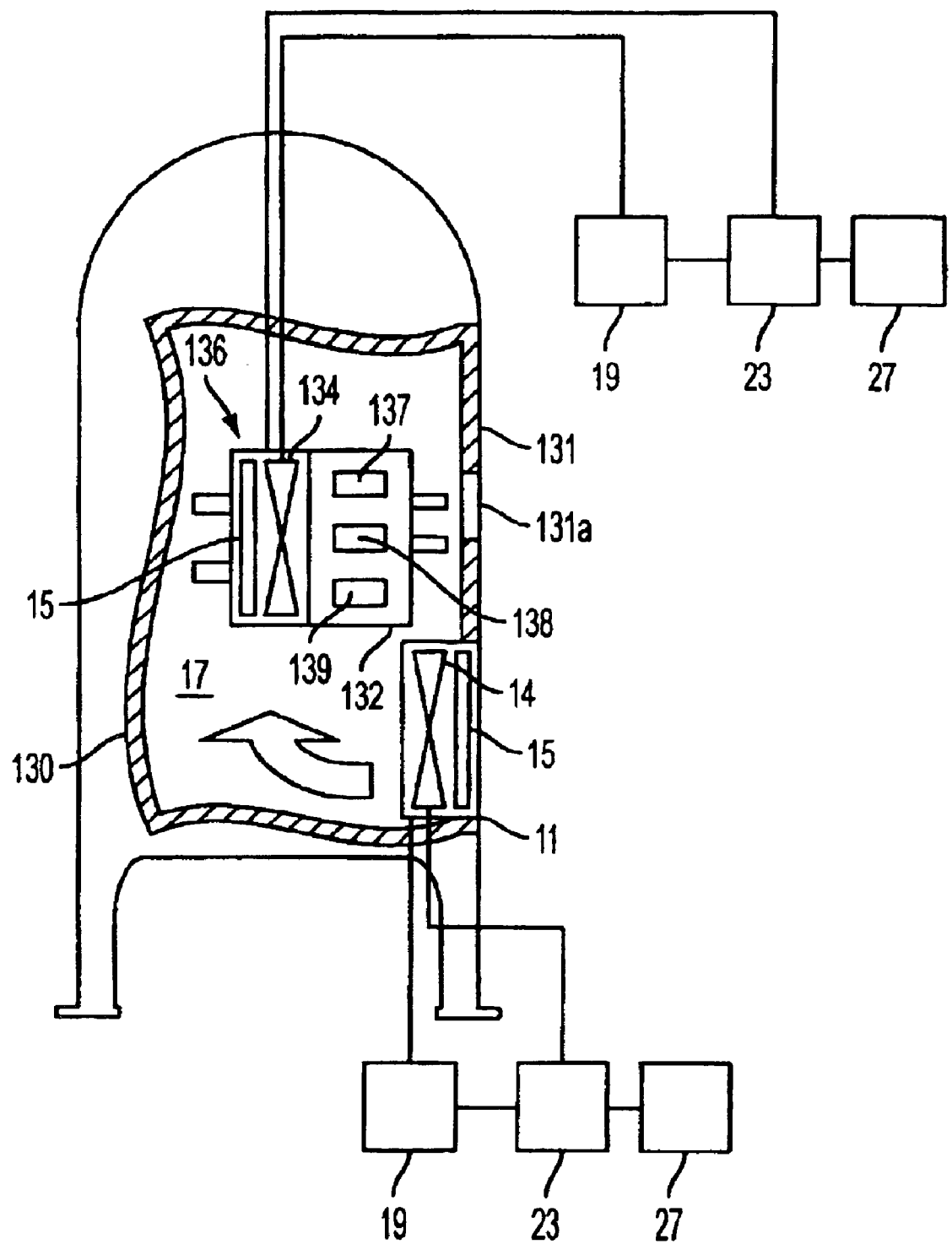
FIG. 2A is a partial frontal sectional view of a conventional mail collection box illustrating a self-contained and removable detection device and system of this invention installed within the mail collection box.

The portable detection system 10 described above for a conventional mail collection box can also be adapted to, for example, a rural, personal, private or business mailbox 100 as shown is FIG. 1D. The preferred embodiment of the system 110 includes a fan 112, an optional filter 113, and a sensor 114 with an alarm 115. For the preferred system 110 to operate effectively, the mailbox 100 can be modified with an air inlet 116 and a sensor port 118. The air inlet 116 and sensor port 118 may further include a conventional one-way valve (not shown) to ensure air within the mailbox 100 is not released into the environment when the fan 112 and sensor 114 are not positioned over or within the air inlet 116 and sensor port 118, respectively. A fan hose or like 120 and a sensor probe, hose, or like 122 are conventionally connected to or inserted into the air inlet 116 and the sensor port 118, respectively. The sensor 114 may alternatively by equipped with a blower 124 to draw the mailbox air into the sensor 114, therefore making the fan 112 optional. Similar to the preferred embodiment of shown in FIG. 1A, a power source connection or power source 126, preferably a battery, are provided for the fan 112 and the sensor 114. A switch 117 and timer 127 may also be provided, similar to the embodiment shown in FIG. 1A. FIG. 2A represents a similar type mail collection box 130 as shown in FIG. 1A. However, in this instance the detection system 132 of the present invention is removably incorporated within mail collection box 130. The fan 134 can be integral to the detection system 132, as shown in FIG. 2A. Prior to the removal of any of the contents of mail collection box 130, a reading is taken of the air within the chamber 17 of mail collection box 130 that has been circulated by an internal fan 134 for sample collection. Additional internal and/or external fans, as illustrated in FIGS 1A and 1B, can be attached or connected to the mail collection box 130 to facilitate air flow to the detection system 132, if necessary. Similarly to the system of FIG. 1A, determination of the presence of hazardous material can be made prior to the removal of the contents of collection container 130. The reading of the air quality can be a visual display 137 (for example, test strip or electronic display) or audible alarm 138 (for example, an alarm) or electronic transmission 139 (for example, a conventional transmitter signals to a conventional remote receiver connected to a conventional controller, such as a personal digital assistant or the like). To observe the visual display 137 from the exterior of the mail collection box 130, a window 131a is placed in a sidewall 131 of the mail collection box 130. The visual display 137 is positioned adjacent the window.

A conventional test strip, which relies upon an anti-body, is generated from a particular bio-agent and will bind to the bio-agent and nothing else. A bio-chemical detector can exploit this phenomenon. Such antibody tests have the added advantage of being able to detect both microorganisms and infectious or hazardous biological toxins, which carry no DNA. In such a case, antibodies are fixed to a strip of cellulose on a plastic backing and can be used to form a reaction between the antibody and the bio-agent which causes colored lines to appear on the strip to indicate the presence of the bio-agent. Such technology is currently available from Tetracore, Inc. Further technology relying upon upconverting phosphor technology is also available.

Figure 2B:
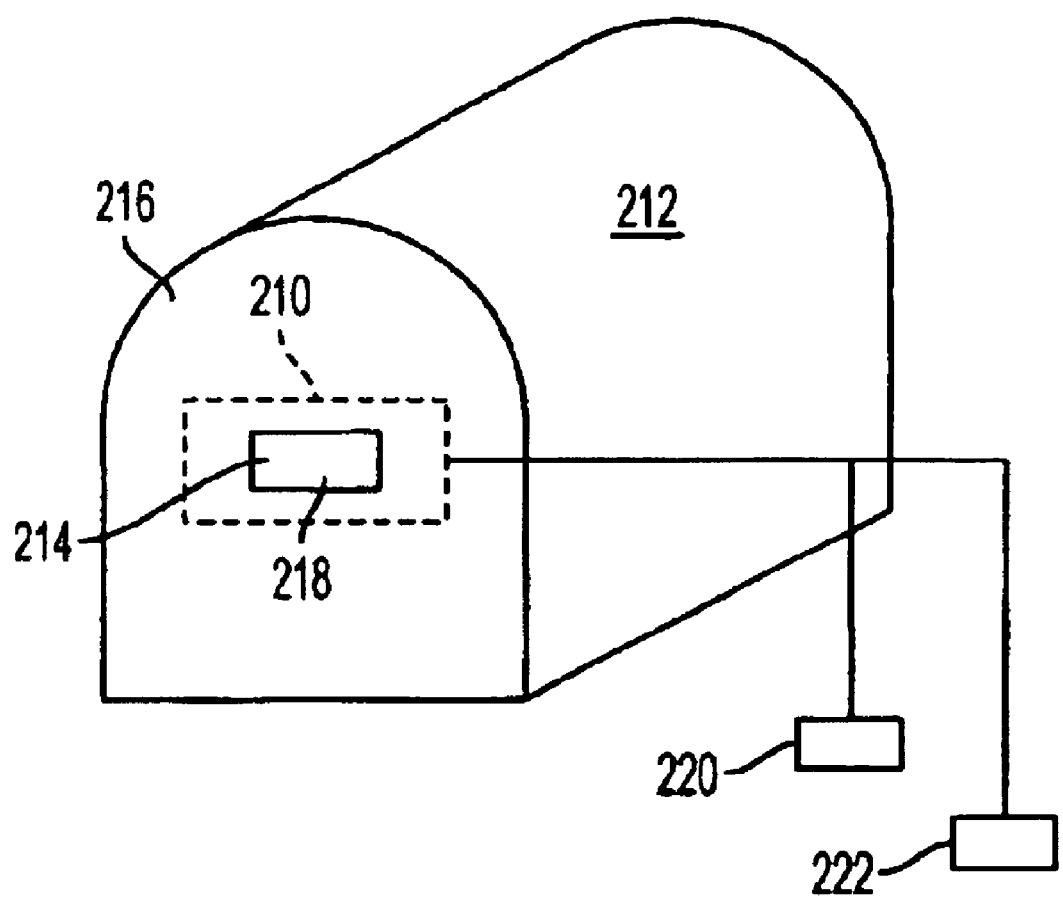
FIG. 2B is a schematic, pictorial representation of a collection container of the type shown in FIG. 1C in which the detection device and system of this invention is self-contained and removably installed within such a container.

FIG. 2B illustrates a removable self-contained detection device 210 for sample collection of a rural, personal, private, or business mailbox 212 or the like similar to the invention illustrated in FIG. 2A. As described for the mail collection box 130, the means for reading of the air quality in the mailbox 212 can be a visual display 218, or audible alarm 220 or an electronic transmitter 222. However, the reading of the particulate concentration must be performed without the reader opening the mailbox 212 as a precaution to possible exposure to an infectious or hazardous biological agent or the possible detonation of an explosive device with a trigger mechanism, for example, sensitive to the slightest motion or light or sound. That means that the visual reading of the air quality must be performed from the exterior of the mailbox 212. To accommodate this requirement a window 214 is installed in a wall 216 of the mailbox 212 with, for example, a test strip 218 being removably attached to the inside surface of the window 214. Similarly, an LCD display or the like can replace the test strip 218 and be positioned in or on the window 214.

Figure 3:
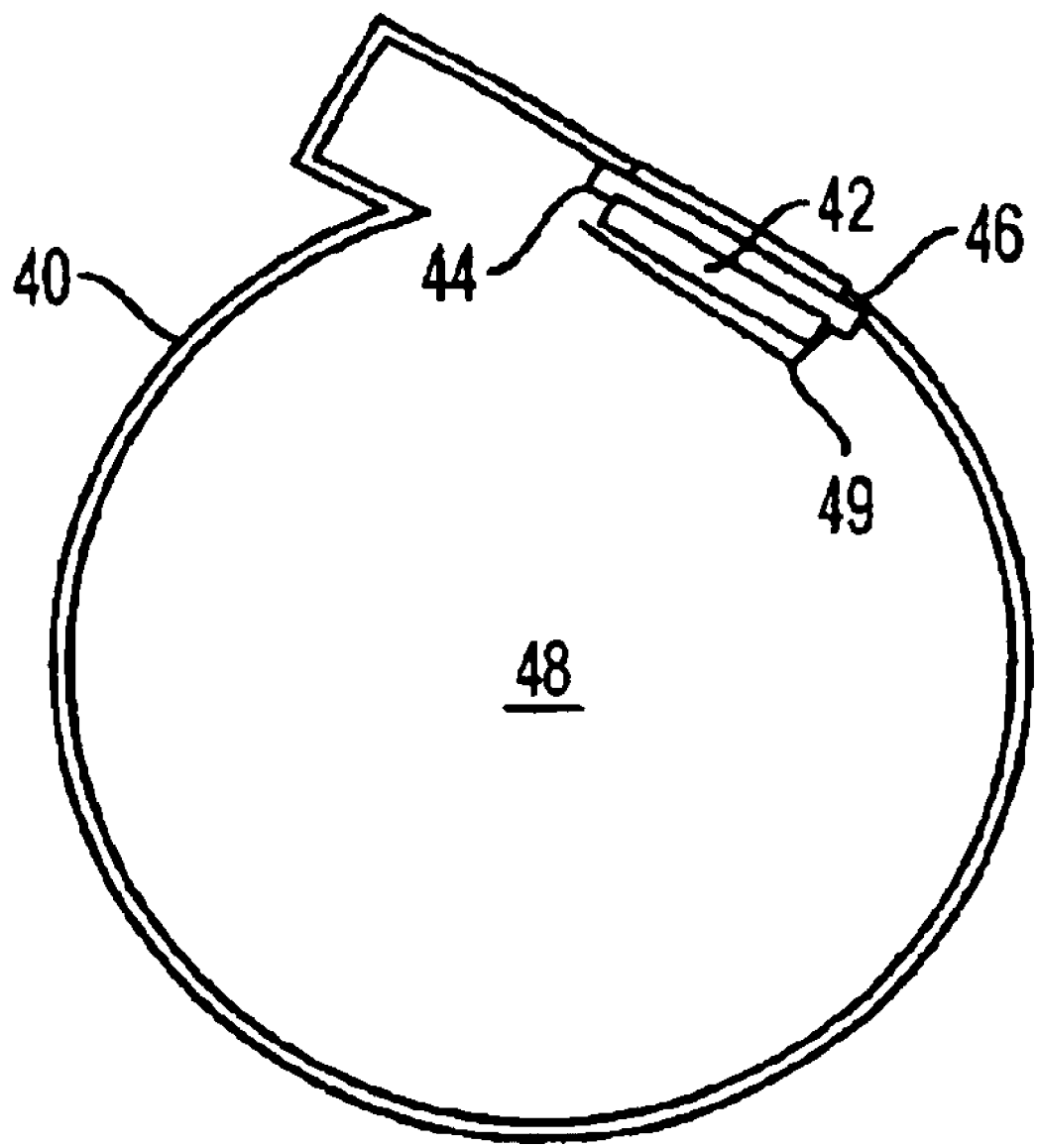
FIG. 3 is a schematic, pictorial representation of a bag or other type container of this invention and which contains therein the detection system of this invention.

FIG. 3 illustrates an embodiment of the present invention in which the contents of a mail collection box or the like has been removed to a test container 40 made up of a bag or box. Container 40 may be transported to the point of removal of the contents of the mail collection box 12 or 30 described above. The container 40 relies upon, for example, a reacting test strip 42 within container 40 having a transparent window 44 such that the hazardous agent detector 42 can be seen from the outside of the container 40. The container 40 includes a cutout 46 to form a viewing port into the interior 48 of the container 40 from the exterior of the container 40. The transparent window 44 is sufficiently larger than the cutout 46 such that the transparent window 44 completely covering the cutout 46. The container 40 and transparent window 44 are of compatible material to adhere or join the transparent window 44 to the container 40, thereby forming a sufficiently airtight seal around the cutout 46. A hazardous agent detector 42 is removably attached by conventional means 49 to the interior of the container adjacent to the transparent window 44. The hazardous agent detector attachment means 49 may include a sleeve on the interior side of the transparent window 44 or a pair of spring clamps or tape or removable glue.

In operation, once mail or other objects to be tested are placed in container 40, vibration or shaking of container 40 manually or by a mechanical system (not shown) contaminates the interior air of container 40 such that the hazardous agent detector 42, for example a test strip, provides an indication of the presence or absence of hazardous material being located within that container 40. Thereafter, upon an indication of a safe container (presence of hazardous material), the contents can be removed to a further location for sorting. Upon the indication of an unsafe container (presence of hazardous material) the contents can also be removed to a further location for further testing prior to sorting thereby preventing its contact with possible future victims. As described above, alternative embodiments to a test strip include a system that activates an audible alarm or electronic signal for transmission to a monitoring station or device.

Figure 4:
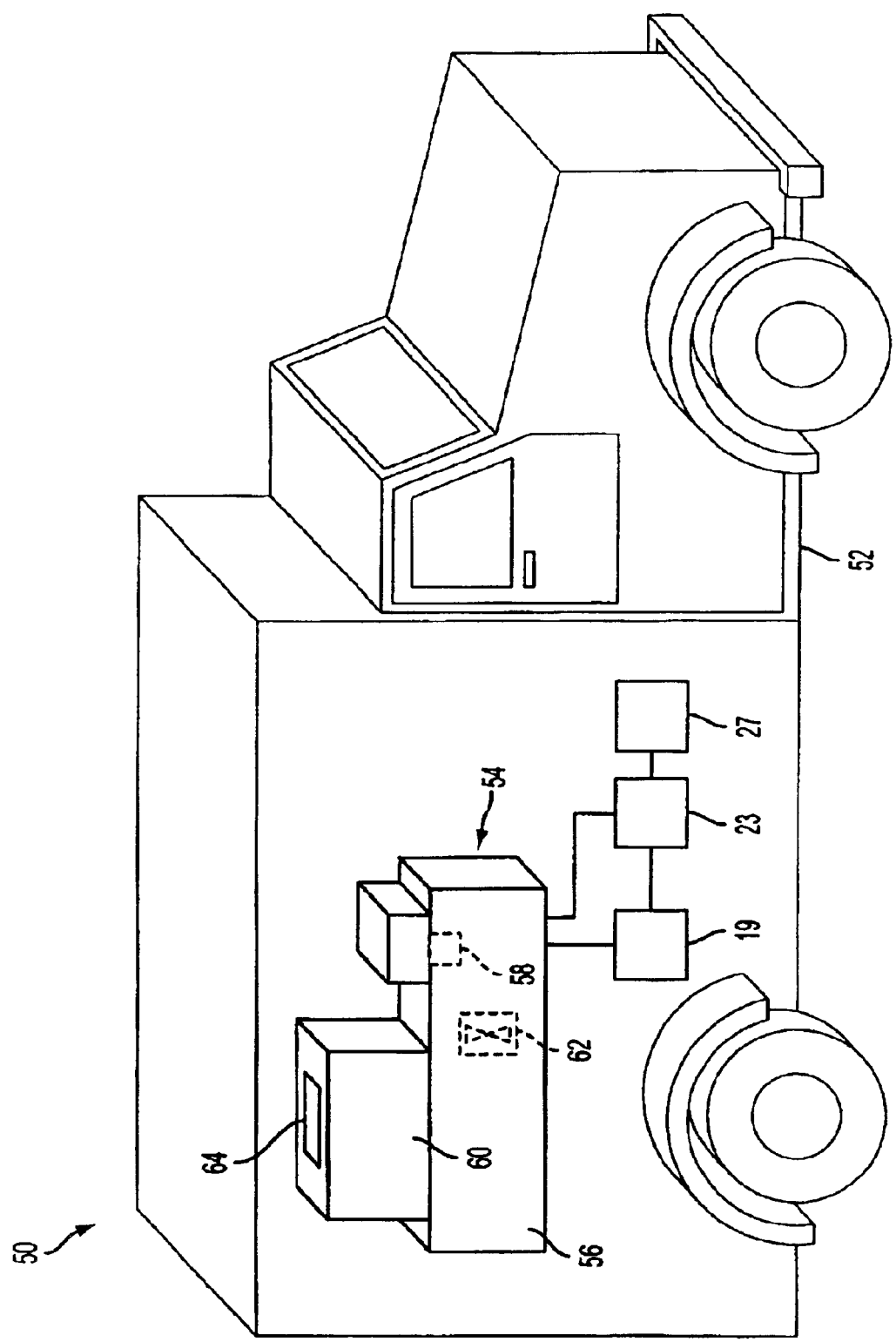
FIG. 4 is a sectional view of a collection vehicle of this invention in which objects to be tested are placed therein within the detection device and system contained with the vehicle.

A fourth embodiment of the present invention relies upon the removal of the mail or objects for its analysis in a portable unit 50 as shown in FIG. 4. The portable unit 50 may be in the form of a collection vehicle 52 or other such movable container that contains therein a detection unit 54. This particular detection unit 54 includes in a test chamber 56, an incoming mail chamber 60, and a detection device 58 to make further tests on the mail or other objects in order to make a determination of their condition prior to the objects removal to another facility. The incoming mail chamber 60 includes at least one door 64 to provide adequate sealing to assure little or no contaminated air leaks outside the detection unit 54 and to assure efficient air circulation within the test chamber 56 such that the detection device 58 receives a sufficient air sample for testing. The detection device 58 is a conventional device similar to those described above. A conventional power source 19, switch 23, and timer 27 can be incorporated into the system 50 as the control system. The power source may include a power connection to the electrical system of the vehicle 52.

In operation, the mail or objects are placed in an incoming mail chamber 60 of the detection unit 54 for controlled delivery of the mail or objects to the test chamber 56. The test chamber 56 includes at least one recirculating fan 62 to agitate the air and loose substances within the test chamber 56 such that the detection device 58 receives a sufficient air sample for testing. Additionally, the vehicle 52 can be driven a distance to supplement the recirculating fan 62 or in place of the recirculating fan 62.

Figure 5:
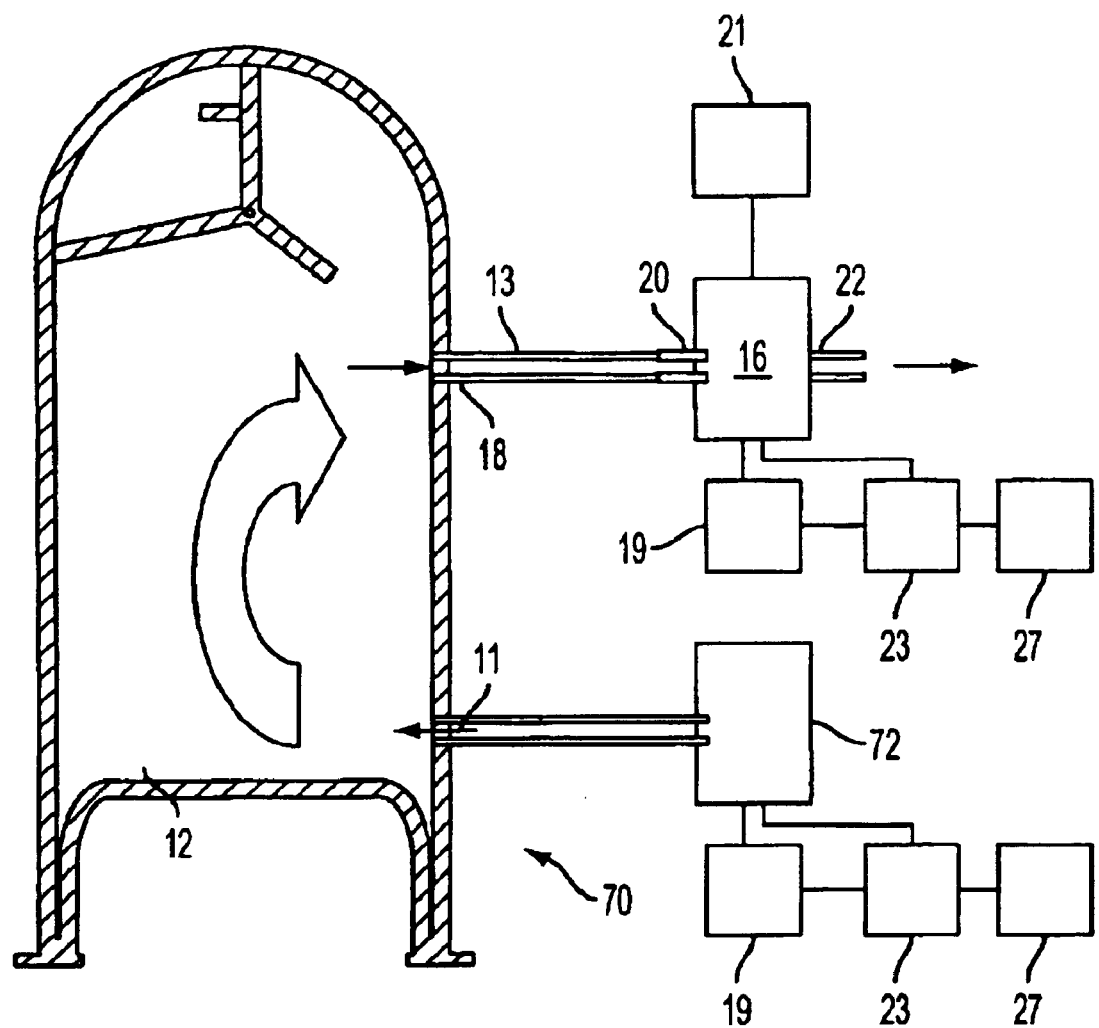
FIG. 5 is a sectional view of a conventional mail collection box illustrating an alternative embodiment of the present invention shown in FIG. 1A with a compressed air source positioned outside the mail collection box in place of the fan.

A further alternative embodiment of the present invention includes a compressed air source as an alternative to a fan 14 to create an air stream or flow within the chamber 17 of the mail collection box. The other system components are the same as those described above and illustrated in FIG. 1A. As shown in FIG. 5, a compressed air source 72 is in fluid communication with the chamber 17 through air inlet 11. The compressed air source 72 can be regulated to supply the appropriate mass flow of air into the chamber 17 to create an air stream to agitate particulates within the chamber 17. Particulates are loosened from deposited objects, and may be released from within the objects when the air stream is strong enough to agitate the objects, as well as the air, to be sampled by the portable detection unit 16. Switches 23, power sources 19, and optional timers 27, similar to the preferred embodiment illustrated in FIG. 1, are used to control air stream and particulate detection device initiation.

It will now be apparent to those skilled in the art that other embodiments, improvements, details, and uses can be made consistent with the letter and spirit of the foregoing disclosure and within the scope of this patent, which is limited only by the following claims, construed in accordance with the patent law, including the doctrine of equivalents.

What is claimed is:

1. In a mailbox having a chamber and a depository port, the improvement comprising a mailbox hazardous material detection system which includes:

air circulation means for creating air-stream in the chamber of the mailbox, said air circulation means being removably attachable to a wall of the mailbox, wherein the air-stream agitates particulates within the mailbox and conveys the particulates for analysis of a hazardous agent; and air sampling means for analyzing air within the chamber for the hazardous agent being removably attachable to the wall of the mailbox and being in fluid communication with the chamber of the mailbox.

2. The system as defined in claim 1, wherein said air circulation means comprises a fan.

3. The system as defined in claim 2, wherein said air circulation means further comprises a filter.

4. The system as defined in claim 1, wherein said air circulation means is capable of being attached to an exterior surface of the mail collection receptacle.

5. The system as defined in claim 1, wherein said air sampling means is capable of being attached to an exterior surface of the mail collection receptacle.

6. In a mail collection receptable having a chamber and a depository port, the improvement comprising a mail receptable hazardous material detection system which includes:

air circulation means for creating an air-stream in the chamber of the mail collection receptacle, said air circulation means being capable of attachment to a wall of the mail collection receptacle, wherein said air-stream agitates particulates within the mail collection receptacle and conveys the particulates for analysis of a hazardous agent, said air circulation means includes a fan; and air sampling means for analyzing air within the chamber for the hazardous agent being capable of attachment to the wall of the mail collection receptacle in fluid communication with the chamber of the mail collection receptacle.

7. The system as defined in claim 2, wherein said air circulation means further comprises a filter.

8. The system as defined in claim 6, wherein said air circulation means is further capable of drawing air from the atmosphere outside the mail collection receptacle to the chamber through an air inlet affixed to the mail collection receptacle.

9. The system of claim 6, wherein said air circulation means is adapted to be located outside the mail collection receptacle and further adapted to force air into the chamber through an inlet port located in the wall of the mail collection receptacle.

10. The system as defined in claim 6, wherein said air circulation means comprises:

a power source connection to power said air circulation means; and an on-off switch operably connected to said power source connection.

11. The system as defined in claim 10, wherein said air circulation means further comprises a timer operably connected to said on-off switch.

12. The system as defined in claim 6, wherein said air sampling means is capable of being attached to an exterior surface of the mail collection receptacle and further adapted to draw air from the chamber through an air outlet affixed to the mail collection receptacle, and further comprises a particulate sensor being capable of sensing the hazardous agents selected from the group consisting of biowarfare agents, chemical agents, and explosive agents, wherein said particulate sensor being further capable of providing an indication whenever said air-stream contains one or more of the hazardous agents.

13. The system as defined in claim 12, wherein said air sampling means comprises:

a power source connection to supply power to said air circulation means; and an on-off switch operably connected to said power source connection.

14. The system as defined in claim 13, wherein said air sampling means further comprises a timer operably connected to said on-off switch.

15. The system as defined in claim 12, wherein said air sampling means further comprises a tube forming a fluid passage between the chamber of the mail collection receptacle and said particulate sensor.

16. The system as defined in claim 6, wherein said air sampling means comprises a particulate sensor being capable of sensing the hazardous agents selected from the group consisting of biowarfare agents, chemical agents, and explosive agents, wherein said particulate sensor being further capable of providing an indication whenever said air-stream contains one or more of the hazardous agents.

17. The system as defined in claim 6, wherein said air circulation means is capable of being attached to an exterior surface of the mail collection receptacle.

18. The system as defined in claim 6, wherein said air sampling means is capable of being attached to an exterior surface of the mail collection receptacle.

19. The system as defined in claim 6, wherein said air circulation means is capable of being attached to an interior surface of the mail collection receptacle.

20. The system as defined in claim 6, wherein said air sampling means is capable of being attached to an interior surface of the mail collection receptacle.

21. In a mail collection receptable having a chamber and a depository port, the improvement comprising a mail collection receptacle hazardous material detection system which includes:

air circulation means for creating an air-stream in the chamber of the mail collection receptacle, said air circulation means being capable of attachment to a wall of the mail collection receptacle, wherein said air-stream agitates particulates within the mail collection receptacle and conveys the particulates for analysis of a hazardous agent, said air circulation means is capable of being attached to an interior surface of the mail collection; and air sampling means for analyzing air within the chamber for the hazardous agent being capable of attachment to the wall of the mail collection receptacle in fluid communication with the chamber of the mail collection receptacle.

22. The system as defined in claim 21, wherein said air circulation means further comprises a filter.

23. The system as defined in claim 21, wherein said air circulation means comprises:

a power source connection to power said air circulation means; and an on-off switch operably connected to said power source connection.

24. The system as defined in claim 23, wherein said air circulation means further comprises a timer operably connected to said on-off switch.

25. The system as defined in claim 21, wherein said air circulation means is further capable of drawing air from the atmosphere outside the mail collection receptacle to the chamber through an air inlet affixed to the mail collection receptacle.

26. The system of claim 21, wherein said air circulation means is adapted to be located outside the mail collection receptacle and further adapted to force air into the chamber through an inlet port located in the wall of the mail collection receptacle.

27. The system as defined in claim 21, wherein said air sampling means is capable of being attached to an exterior surface of the mail collection receptacle and further adapted to draw air from the chamber through an air outlet affixed to the mail collection receptacle, and further comprises a particulate sensor being capable of sensing the hazardous agents selected from the group consisting of biowarfare agents, chemical agents, and explosive agents, wherein said particulate sensor being further capable of providing an indication whenever said air-stream contains one or more of the hazardous agents.

28. The system as defined in claim 27, wherein said air sampling means comprises:
   a power source connection to supply power to said air circulation means; and
   an on-off switch operably connected to said power source connection.

29. The system as defined in claim 28, wherein said air sampling means further comprises a timer operably connected to said on-off switch.

30. The system as defined in claim 27, wherein said air sampling means further comprises a tube forming a fluid passage between the chamber of the mail collection receptacle and said particulate sensor.

31. The system as defined in claim 21, wherein said air sampling means comprises a particulate sensor being capable of sensing the hazardous agents selected from the group consisting of biowarfare agents, chemical agents, and explosive agents, wherein said particulate sensor being further capable of providing an indication whenever said air-stream contains one or more of the hazardous agents.

32. In a mail collection receptacle having a chamber and a depository port, the improvement comprising a mail collection receptacle hazardous material detection system which includes:
   air circulation means for creating an air-stream in the chamber of the mail collection receptacle, said air circulation means being capable of attachment to a wall of the mail collection receptacle, wherein said air-stream agitates particulates within the mail collection receptacle and conveys the particulates for analysis of a hazardous agent; and
   air sampling means for analyzing air within the chamber for the hazardous agent being capable of attachment to the wall of the mail collection receptacle in fluid communication with the chamber of the mail collection receptacle, said air sampling means is capable of being attached to an interior surface of the mail collection receptacle.

33. The system as defined in claim 32, wherein said air sampling means is constructed and arranged to be monitored through a transparent window affixed to the mail collection receptacle.

34. The system as defined in claim 33, wherein said air sampling means comprises a test strip.

35. The system as defined in claim 32, wherein said air circulation means further comprises a filter.

36. The system as defined in claim 32, wherein said air circulation means comprises:
   a power source connection to power said air circulation means; and
   an on-off switch operably connected to said power source connection.

37. The system as defined in claim 36, wherein said air circulation means further comprises a timer operably connected to said on-off switch.

38. The system as defined in claim 32, wherein said air circulation means is further capable of drawing air from the atmosphere outside the mail collection receptacle to the chamber through an air inlet affixed to the mail collection receptacle.

39. The system as defined in claim 32, wherein said air circulation means is adapted to be located outside the mail collection receptacle and further adapted to force air into the chamber through an inlet port located in the wall of the mail collection receptacle.

40. The system as defined in claim 32, wherein said air sampling means is capable of being attached to an exterior surface of the mail collection receptacle and further adapted to draw air from the chamber through an air outlet affixed to the mail collection receptacle, and further comprises a particulate sensor being capable of sensing the hazardous agents selected from the group consisting of biowarfare agents, chemical agents, and explosive agents, wherein said particulate sensor being further capable of providing an indication whenever said air-stream contains one or more of the hazardous agents.

41. The system as defined in claim 40, wherein said air sampling means comprises:
   a power source connection to supply power to said air circulation means; and
   an on-off switch operably connected to said power source connection.

42. The system as defined in claim 41, wherein said air sampling means further comprises a timer operably connected to said on-off switch.

43. The system as defined in claim 40, wherein said air sampling means further comprises a tube forming a fluid passage between the chamber of the mail collection receptacle and said particulate sensor.

44. The system as defined in claim 32, wherein said air sampling means comprises a particulate sensor being capable of sensing the hazardous agents selected from the group consisting of biowarfare agents, chemical agents, and explosive agents, wherein said particulate sensor being further capable of providing an indication whenever said air-stream contains one or more of the hazardous agents.

* * * * *

UNITED STATES PATENT AND TRADEMARK OFFICE
CERTIFICATE OF CORRECTION

PATENT NO. : 6,948,653 B2
DATED : September 27, 2005
INVENTOR(S) : Beckert et al.

It is certified that error appears in the above-identified patent and that said Letters Patent is hereby corrected as shown below:

<u>Title page,</u>
Item [56], References Cited, OTHER PUBLICATIONS, should include:
-- International Search Report, Oct. 17, 2003, PCT/US02/35984 (12078-154PCT). --.

Signed and Sealed this

Thirteenth Day of December, 2005

JON W. DUDAS
*Director of the United States Patent and Trademark Office*